United States Patent
Davis

(10) Patent No.: US 6,942,372 B1
(45) Date of Patent: Sep. 13, 2005

(54) HEAT DISSIPATING TURRET FOR FIBEROPTIC ILLUMINATOR

(76) Inventor: James M. Davis, 4424 Corporate Square Dr., Naples, FL (US) 34104

(*) Notice: Subject to any disclaimer, the term of this patent is extended or adjusted under 35 U.S.C. 154(b) by 112 days.

(21) Appl. No.: 10/444,673

(22) Filed: May 23, 2003

Related U.S. Application Data

(60) Provisional application No. 60/382,768, filed on May 23, 2002.

(51) Int. Cl.[7] ............................................. F21V 29/00
(52) U.S. Cl. ...................... 362/580; 362/294; 362/581; 385/58; 385/70
(58) Field of Search ................................ 362/294, 554, 362/572, 573, 574, 580, 581; 385/53, 85, 385/92, 70, 58

(56) References Cited

U.S. PATENT DOCUMENTS

| | | | |
|---|---|---|---|
| 5,230,555 A * | 7/1993 | Stephenson et al. | 362/572 |
| 5,243,500 A * | 9/1993 | Stephenson et al. | 362/580 |
| 5,283,718 A * | 2/1994 | Stephenson et al. | 362/572 |
| 5,695,275 A * | 12/1997 | Markiewicz et al. | 362/294 |
| 5,882,102 A * | 3/1999 | Pileski | 362/554 |
| 6,409,391 B1 * | 6/2002 | Chang | 385/53 |
| 6,626,582 B2 * | 9/2003 | Farrar et al. | 385/53 |

* cited by examiner

*Primary Examiner*—John Anthony Ward
(74) *Attorney, Agent, or Firm*—William E. Noonan

(57) ABSTRACT

A heat dissipating turret for a fiberoptic illuminator includes first turret component composed of a heat conducting material and a second turret component composed of a heat insulating material. The first turret component is releasably interengaged with the front panel of the illuminator and the second turret component is releasably attached to the first turret component. The turret components include respective interior light transmitting channels that communicate when the components are interengaged. The second turret component includes a receptacle for receiving the end fitting of a fiberoptic cable. Light from the illuminator is transmitted through the communicating channels to the fiberoptic cable and the turret components dissipate heat that is generated at the focal point of the illuminator.

11 Claims, 2 Drawing Sheets

US 6,942,372 B1

HEAT DISSIPATING TURRET FOR FIBEROPTIC ILLUMINATOR

RELATED APPLICATION

This application claims the benefit of U.S. Provisional Application Ser. No. 60/382,768, filed May 23, 2002.

FIELD OF THE INVENTION

This invention relates to a turret or outlet port for fiberoptic illuminator and, more particularly, to a two-part turret that significantly reduces the amount of heat transmitted from the illuminator to an attached fiberoptic cable.

BACKGROUND OF THE INVENTION

Fiberoptic illuminators are employed widely in medical, dental and surgical procedures. The illuminator housing encloses a relatively high intensity light source. Metal halide, xenon and halogen light sources are commonly utilized. A fiberoptic cable is connected to a turret or output port mounted on the front panel of the illuminator. Light from the light source is directed through the turret to a focal point located within the turret at or close to the inlet end of the attached fiberoptic cable. The cable conducts the light and delivers it to an attached headlamp or analogous equipment. The light output is then used, as needed, for a particular medical procedure or application.

The heat generated by the illuminator at the focal point is typically extremely intense. In conventional illuminators, the turret is composed of a heat conducting metal or metal alloy. As a result, the turret transmits the intense heat at the focal point to the attached fiberoptic cable, as well as to the front panel of the illuminator housing. During a medical or surgical procedure using the illuminator, the doctor, nurse, technician or other medical personnel operating the equipment may have to touch the inlet end of the fiberoptic cable and/or the front panel of the illuminator. Such persons risk being seriously burned by the intense heat that is generated by the illuminator. To date, there are no known illuminator turrets which effectively dissipate this heat and reduce the danger of the user being seriously hurt.

SUMMARY OF THE INVENTION

It is therefore an object of the present invention to provide a heat dissipating turret for a fiberoptic illuminator which effectively reduces the heat that is transmitted by the illuminator to the front panel of the illuminator housing and to an attached fiberoptic cable.

It is a further object of this invention to provide a heat dissipating illuminator turret, which significantly reduces the risk that personnel operating the illuminator and/or attached fiberoptic cable will be burned or injured.

It is a further object of this invention to provide a heat dissipating illuminator turret which is convenient to assemble and disassemble, and which accommodates a variety of fiberoptic cable plugs.

It is a further object of this invention to provide a heat dissipating illuminator turret which may be quickly and conveniently modified to engage a selected type of fiberoptic cable plug with the illuminator.

This invention results from a realization that the intense heat generated at the focal point of a fiberoptic illuminator may be effectively dissipated by constructing the light output turret using a two part metal/plastic assembly. This type of construction maintains its rigidity but also dissipates heat far more effectively than conventional turrets.

This invention features a heat dissipating turret for operably interengaging a fiberoptic cable to a fiberoptic illuminator. The turret includes a first turret component composed of a heat conducting metallic material. The first turret component is releasably attached to a light output opening of the illuminator. The first component has a light conducting channel formed therethrough. There is also a second turret component composed of a heat insulating, non-metallic material. There is a second light conducting channel formed through the second turret component. The first and second turret components are interengaged such that the first and second light conducting channels communicate to transmit light from the illuminator therethrough. The second turret component includes an outlet port that is releasably interengaged by an input end fitting of the fiberoptic cable such that light is transmitted from the illuminator through the first and second channels of the first and second turret components respectively and into the interengaged inlet fitting of the fiberoptic cable.

In a preferred embodiment, the first and second turret components are releasably interengaged by means of complementary threads. The first turret component may be threadably engaged with the illuminator housing. One or both of the turret components may include heat dissipating fins, which may be formed circumferentially about the respective components. The first turret component may be composed of aluminum and the second turret component may constitute Delryn™ or an analogous insulating plastic material. Each of the turret components may include a circumferential knurled portion adjacent to a respective set of circumferential fins. The second turret portion may include a spring biased locking mechanism for holding an attached fiberoptic cable end fitting in place within the turret.

DETAILED DESCRIPTION OF PREFERRED EMBODIMENTS

Other objects, features and advantages will occur from the following description of a preferred embodiment and the accompanying drawings, in which.

Figure 1:
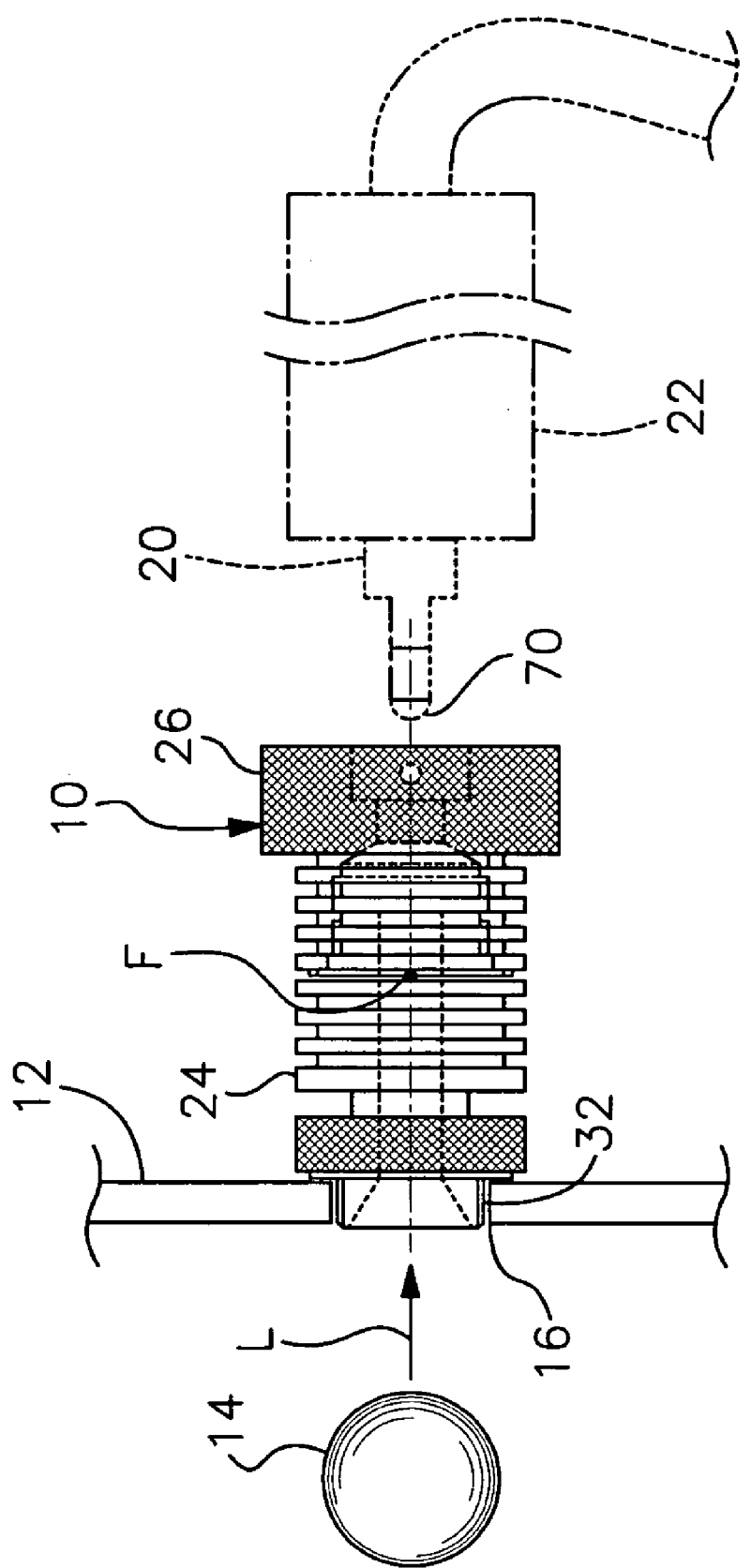
FIG. 1 is an elevational side view, partly in schematic, of a fiberoptic cable which is operably attached to an illuminator through the heat dissipating turret of this invention.

There is shown in FIG. 1 a heat dissipating turret 10 that is operably mounted to the front panel 12 of a standard fiberoptic illuminator. The particular details of the illuminator are well known and not shown herein. A light source 14, typically comprising a metal halide, xenon and halogen bulb, is mounted in a conventional manner within the illuminator housing. It should be understood that various alternative types of fiberoptic light sources may be employed within the scope of this invention. The light source is mounted within the housing in any variety of ways which will be known to persons skilled in the art. In operation, light L from light source 14 is directed through an outlet or opening 16 formed in illuminator panel 12 and is directed to a focal point F, which is traditionally located within a turret attached to outlet 16. The focal point is typically located at or close to the entrance or inlet and of an attached fiberoptic cable 22. As previously stated, conventional turrets are composed entirely of metal and become extremely hot as a result of the heat generated at the focal point.

Turret 10 is releasably attached to illuminator panel 12 and is operably interengaged by the end fitting 20 of fiberoptic cable 22. As with the illuminator, cable 22 does not comprise a part of this invention. Various types of cables may be employed with and attached to turret 10 within the scope of the invention.

Figure 2:
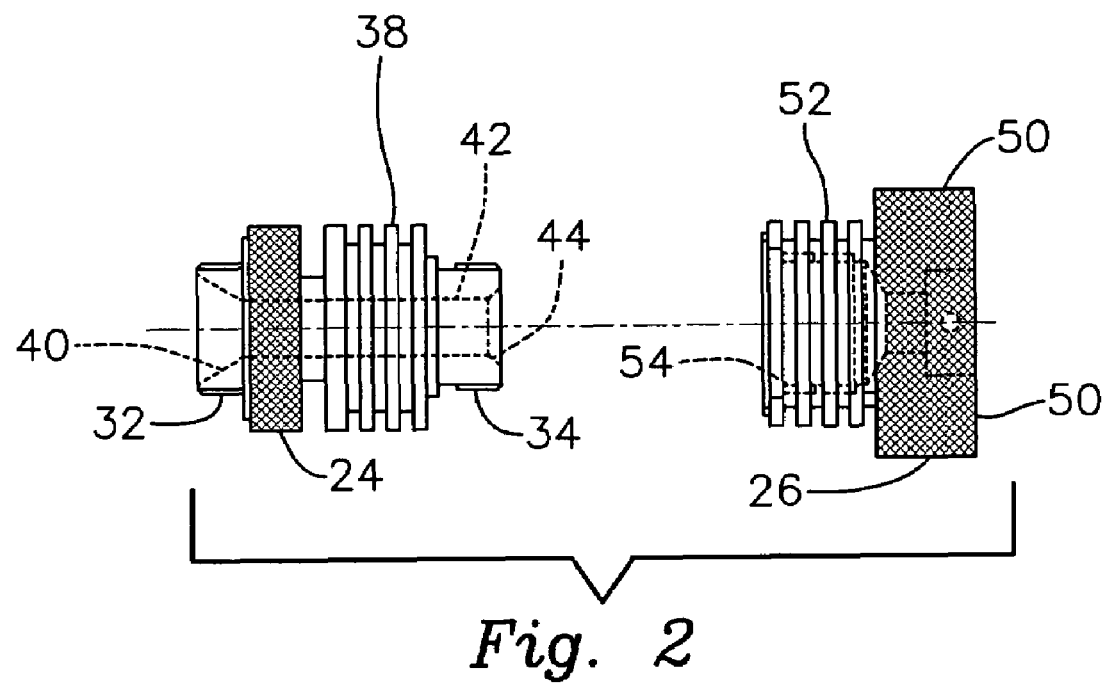
FIG. 2 is an elevational side view of the first and second turret components.
Figure 3:
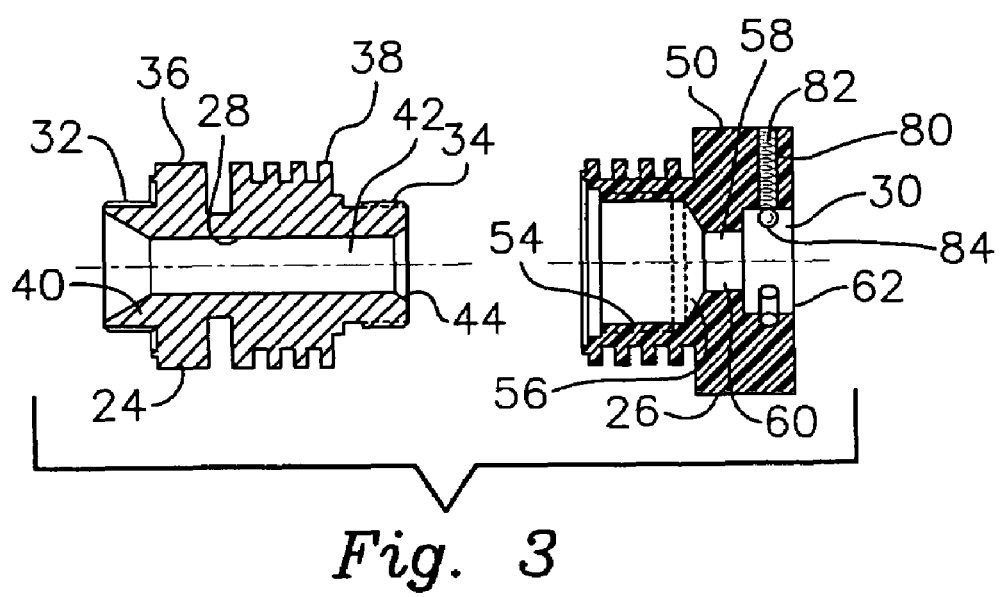
FIG. 3 is an elevational, cross sectional view of the turret components.

Turret 10 includes first and second turret components 24 and 26 which are shown operably interconnected in FIG. 1 but in a separated condition in FIGS. 2 and 3. First turret component 24 includes a first light conducting central channel 28; and turret component 26 similarly includes a second light conducting central channel 30. The light conducting channels extend through their respective turret components from one end to the other. Turret component 24 is typically composed of aluminum or some other thermally conductive type of metal or metal alloy. Conversely, second turret component 26 is composed of a thermally insulating plastic such as Delryn™. Each of the components features a generally circular cross-sectional shape when viewed from either end of the component.

Aluminum component 24 includes an exteriorly threaded inlet end 32 and an interiorily threaded outlet end 34. An annular knurled portion 36 is located adjacent to threaded inlet portion 32. This knurled portion is formed circumferentially about component 24. A series of circumferential ribs or fins 38 are formed between knurled portion 36 and threaded outlet end 34. Interior channel 28 of component 24 includes a convergingly tapered entrance 40, an elongate bore 42 and a divergingly tapered exit 44.

Second component 26 includes its own circumferential knurled portion 50. A second series of heat dissipating fins 52 are formed circumferentially about component 26 adjacent to and inwardly of knurled portion 50. The interior channel 30 of component 26 includes several discrete sections. In particular, there is a relatively large mouth section 54 that has interior threads, which are operably interengagable with the threads of outlet portion 34 on component 24. A tapered portion 56 interconnects threaded mouth 54 with a reduced diameter section 58. This reduced diameter section and forms an inner part of receptacle 60 for receiving an attached fiberoptic cable end fitting. The receptacle also includes a relatively large diameter section 62, which is formed proximate the outlet (i.e. right-hand) end of component 26.

In operation, aluminum turret component 24 is mounted to the front panel 12 of the fiberoptic illuminator. This is accomplished by threadably engaging section 32 of component 24 with complementary threads carried about opening 16 of the illuminator.

Insulating plastic turret component 26 is then threadably interengaged with first component 24. It should be understood that this may also be accomplished before the first turret component is threadably mounted onto the front panel of the illuminator. In either case, second turret portion 26 is threaded onto first portion 24 such that threaded mouth 54 operably interengages threaded outlet 34. The outlet end of component 24 is received within the mouth 54 of component 26. The attached turret components appear as shown in FIG. 1. Interior channel 28 of component 24 optically communicates with interior channel 30 of component 26. Inlet end fitting 20 of fiberoptic cable 22 is inserted into complementary, conformably shaped receptacle 62 of turret component 26. This places the inlet end 70 of fitting 20 at or proximate to focal point F within the communicating channels of the attached turret components.

Fiberoptic illumination is performed for a desired medical, dental or surgical task. Specifically, the light L from illuminator bulb 14 is directed through the communicating central channels of turret 10 to focal point F. The light then enters inlet 70 of fiberoptic cable 22 and is transmitted to a selected piece of illuminating equipment attached to the other end of the cable. The intense heat generated at focal point F is transmitted to turret 10 and is effectively dissipated or reduced by the turret. Specifically, heat is absorbed by the walls of aluminum component 24; however, the insulating material of Delryn™ component 26 blocks a substantial portion of this heat from being transmitted to the attached fiberoptic cable end fitting 20. Heat is further dissipated by the circumferential fins 38 and 52 of components 24 and 26 respectively. End fitting 20 and cable 22, as well as panel 12, remain relatively cool. Medical personnel are able to handle cable 22 and attached end fitting 20 safely and conveniently with much reduced risk of suffering burns and injury. Likewise, the front of the illuminator panel may be touched safely.

I have determined that the turret operates most effectively when it employs both a metal (heat conductive) and nonmetallic (heat insulating) components as described herein. If the entire turret is composed of Delryn™ or analogous material, the heat generated at the focal point will tend to soften and weaken the structure of the turret thereby reducing its effectiveness considerably. Utilizing the two-part construction of this invention allows the conductive metal components to act effectively as a heat sink which absorbs much of the heat. The insulting Delryn™ component largely blocks the transmission of this heat to components of the attached fiberoptic cable.

It should also be understood that the second insulating turret component may feature a plurality of alternatively configured receptacles which are capable of interengaging various varieties of standard fiberoptic cables. The receptacle 30 disclosed herein accommodates a StorZ™ end fitting. Other alternatively shaped receptacles may be utilized for engaging complementarily shaped end fittings used in other types of cable.

A releasably locking mechanism is optionally employed for holding the fiberoptic cable end fitting in secure interengagement with turret 10. This is shown, for example, in the drawings which illustrate a plurality of spring biased ball plungers 80 formed radially about section 62 of receptacle 60. Three such ball plungers are typically mounted within component 26. Each ball plunger includes a spring 82, FIG. 3, which urges a bearing 84 into interengagement with an attached end fitting. When the end fitting of the fiberoptic cable is inserted into the receptacle, the bearings 84 are pushed outwardly against their respective springs 82. The bearings retract and the end fitting is inserted into the receptacle. The springs then urge the bearings against the end fitting to hold the end fitting securely in place within receptacle 60. The ball plungers comprise known devices for holding fiberoptic cables releasably in place within illuminator outlet ports or turrets. Various types of ball plungers or similar devices may be employed to perform this releasable locking function.

Accordingly, the present invention features a heat dissipating turret for use in attaching a fiberoptic cable to a fiberoptic illuminator. The use of a non-conductive component that is attached to a conductive turret component effectively blocks the transmission of heat from the focal point of the illuminator to other parts of the light source. At the same time, the aligned communicating channels 28 and 30 permit light to be effectively transmitted from the light source to the inlet end of the cable. An effective illuminator is achieved but at the same time operator safety is improved considerably.

It should be understood that in still other embodiments of this invention the light may be conducted through the turret by means other then the channels disclosed herein. For example, a glass fiber or light pipe extend from the inlet end of component 24 to a location at or proximate to the focal point F. The light may be transmitted by such a fiber to the focal point and then delivered to the attached fiberoptic cable end fitting in a manner similar to that described above.

The use of the threaded, two-part construction described above is particularly effective for permitting the turret to be adapted effectively and conveniently for use with different types of fiberoptic cables and end fittings. For example, if use of a different brand of cable is required, the user may simply disengage second turret component 26 from first turret component 24. An alternative heat insulating turret component having a receptacle configuration that complements the new selected fiberoptic cable may then be attached to component 24. The alternative heat insulating component may have a threaded mouth shaped identically to mouth 54. However, the receptacle may be altered to complement the type of fiberoptic cable end fitting which is to be used. A virtually endless variety of configurations may be employed for the second turret component.

Likewise, the first turret component (and thereby the entire turret) may be quickly and conveniently disengaged from the front panel of the illuminator by simply unscrewing end portion 32 from panel 12. The turret can then be replaced by an alternatively shaped turret as required. It should be understood that the turret components may be interengaged by means other then threads (e.g. by friction fit, etc.).

From the foregoing it may be seen that the apparatus of this invention provides for turret or outlet port for fiberoptic illuminator and, more particularly, to a two-part turret that significantly reduces the amount of heat transmitted from the illuminator to an attached fiberoptic cable. While this detailed description has set forth particularly preferred embodiments of the apparatus of this invention, numerous modifications and variations of the structure of this invention, all within the scope of the invention, will readily occur to those skilled in the art. Accordingly, it is understood that this description is illustrative only of the principles of the invention and is not limitative thereof.

Although specific features of the invention are shown in some of the drawings and not others, this is for convenience only, as each feature may be combined with any and all of the other features in accordance with this invention.

What is claimed:

1. A heat dissipating turret for operably engaging a fiberoptic cable to a fiberoptic illuminator housing, which illuminator housing includes a light output opening, said turret comprising;

a first turret component composed of a heat conducting metallic material and having a first light conducting channel formed therethrough, and a second turret component composed of a heat insulating, non-metallic material and including a second light conducting channel formed therethrough, said first and second turret components being interengaged and said first turret component being attachable to the illuminator housing such that said first light conducting channel communicates with the light output opening of the illumination housing and said first and second light conducting channels communicate to transmit light from the illuminator housing through said light conducting channels; said second turret having an outlet post communicating with said second light conducting channel and being releasably interengagable by an input fitting of the fiberoptic cable, whereby light is transmittable from the illuminator through the interengaged turret components to an interengaged fiberoptic cable.

2. The device of claim 1 in which said first turret component is releasably engagable with the illuminator housing.

3. The device of claim 1 in which said first and second turret components are releasably interengaged.

4. The device of claim 3 in which said first and second turret components include complementary threads for releasably interengaging said first and second turret components.

5. The device of claim 2 in which said first turret component includes a first threaded section for releasably interengaging a corresponding threaded section of the illuminator housing to releasably engage said first threaded section with the illuminator housing.

6. The device of claim 1 in which at least one of said turret components includes heat dissipating fins.

7. The device of claim 1 in which at least one of said turret components has a cylindrical section and a series of heat dissipating fins formed circumferentially about said cylindrical section.

8. The device of claim 1 in which said first turret component is composed of aluminum.

9. The device of claim 1 in which said second turret component is composed of a thermally insulating plastic.

10. The device of claim 1 in which at least one of said turret components includes an annular part having a knurled circumferential surface.

11. The device of claim 1, in which said second turret component includes a spring biased locking mechanism for holding an attached fiberoptic cable end fitting in place within said outlet port of said second turret component.

\* \* \* \* \*